(12) United States Patent
Kampa-Schittenhelm et al.

(10) Patent No.: US 9,079,938 B2
(45) Date of Patent: Jul. 14, 2015

(54) ASPP2 SPLICING VARIANT

(71) Applicant: Eberhard-Karls-Universit•t Tübingen Universit•tsklinikum, Tübingen (DE)

(72) Inventors: Kerstin Kampa-Schittenhelm, Tübingen (DE); Marcus Schittenhelm, Tübingen (DE)

(73) Assignee: Eberhard-Karls-Universität Tübingen Universitätsklinikum, Tuebingen (DE)

( * ) Notice: Subject to any disclaimer, the term of this patent is extended or adjusted under 35 U.S.C. 154(b) by 0 days.

(21) Appl. No.: 13/753,354

(22) Filed: Jan. 29, 2013

(65) Prior Publication Data

US 2013/0129736 A1 May 23, 2013

Related U.S. Application Data

(63) Continuation of application No. PCT/EP2011/063283, filed on Aug. 2, 2011.

(30) Foreign Application Priority Data

Aug. 2, 2010 (DE) .................. 10 2010 033 575

(51) Int. Cl.
*G01N 33/574* (2006.01)
*G01N 33/577* (2006.01)
*C07K 7/06* (2006.01)
*C07K 14/47* (2006.01)
*C12Q 1/68* (2006.01)

(52) U.S. Cl.
CPC .............. *C07K 7/06* (2013.01); *C07K 14/4747* (2013.01); *C12Q 1/6886* (2013.01); *G01N 33/57426* (2013.01); *C12Q 2600/156* (2013.01); *C12Q 2600/158* (2013.01); *G01N 2333/4704* (2013.01); *G01N 2800/50* (2013.01)

(58) Field of Classification Search
None
See application file for complete search history.

(56) References Cited

U.S. PATENT DOCUMENTS

| | | | |
|---|---|---|---|
| 5,977,311 | A | 11/1999 | Nandabalan et al. |
| 7,081,340 | B2 | 7/2006 | Baker et al. |
| 2002/0086384 | A1 | 7/2002 | Levine et al. |
| 2002/0197243 | A1* | 12/2002 | Nicolette ................ 424/93.21 |
| 2003/0225528 | A1 | 12/2003 | Baker et al. |
| 2006/0099202 | A1 | 5/2006 | Nicolette et al. |
| 2011/0086349 | A1* | 4/2011 | Anjomshoaa et al. ............ 435/6 |

FOREIGN PATENT DOCUMENTS

| | | |
|---|---|---|
| WO | WO 99/15657 | 4/1999 |
| WO | WO 03/078662 | 9/2003 |
| WO | WO 2004/074518 | 9/2004 |
| WO | WO2006086111 | * 8/2006 |

OTHER PUBLICATIONS

Bignon, Genetic Predisposition to Cancer, Second Edition, p. 11-20, 2004.*
Brawer, Urology, vol. 52, p. 372-378, 1998.*
Budman, CUAJ, vol. 2, No. 3, p. 212-221.*
Ludwig, Nature Reviews Cancer, vol. 4, p. 845-856, 2005.*
Mettlin, Cancer, vol. 74, p. 1615-1620, 1994.*
Pepe, Journal of the National Cacner Institute, vol. 93, No. 14, p. 1054-1061, 2001.*
Bergamaschi et al., "ASPP1 and ASPP2: Common activators of p53 family members," *Molecular and Cellular Biology* 24:1341-1350 (Feb. 2004).
Bergamaschi et al., "iASPP oncoprotein is a key inhibitor of p53 conserved from worm to human," *Nature Genetics* 33:162-167 (2003).
Gorina and Pavletich, "Structure of the p53 Tumor Suppresser Bound to the Ankyrin and SH3 Domains of 53BP2," *Science* 274:1001-1005 (Nov. 8, 1996).
International Preliminary Report on Patentability from the parent PCT Application No. PCT/EP2011/063283 (in German with English language translation), (dated Aug. 2, 2010).
Iwabuchi et al., "Two cellular proteins that bind to wild-type but not mutant p53," *Proceedings of the National Academy of Science USA* 91:6098-6102 (Jun. 1994).
Kampa et al., "Apoptosis-stimulating protein of p53 (ASPP2) heterozygous mice are tumor-prone and have attenuated cellular damage-response thresholds," *Proceedings of the National Academy of Science USA* 106(11):4390-4395 (Mar. 17, 2009).
Kampa et al., "New insights into the expanding complexity of the tumor suppressor ASPP2," *Cell Cycle* 8:2871-2876 (Sep. 15, 2009).
Naumovski and Cleary, "The p53-binding protein 53BP2 also interacts with Bcl2 and impedes cell cycle progression at $G_2/M$," *Molecular and Cellular Biology* 16:3884-3892 (Jul. 1996).
Printout: www.ncbi.nlm.nih,gov/gene?term=p53BP2 for "TP53BP2: tumor protein p53binding protein," (Jun. 9, 2011).
Samueles-Lev et al., "ASPP proteins specifically stimulate the apoptotic function of p53," *Molecular Cell* 8:781-794 (Oct. 2001).
Takahashi et al., "Expression of 53BP2 and ASPP2 proteins from TP53BP2 gene by alternative splicing," *Biochemical and Biophysical Research Communications* 315:434-438 (2004).
Trigiante and Lu, "ASPPs and cancer," *Nature Reviews/Cancer* 6:217-227 (2006).
Vives et al., "ASPP2 A gene that controls life and death in vivo," *Cell Cycle* 5(19):2187-2190 (Oct. 1, 2006).
Vives et al., "ASPP2 is a haploinsufficient tumor suppressor that cooperates with p53 to suppress tumor growth," *Genes and Development* 20:1262-1267 (2006).

* cited by examiner

*Primary Examiner* — Mark Halvorson
*Assistant Examiner* — Michael D Allen
(74) *Attorney, Agent, or Firm* — Klarquist Sparkman, LLP

(57) ABSTRACT

The present invention relates to a method for the in vitro determination of the presence of or a predisposition of a patient to the development of cancer. In the method according to the invention, the presence of a marker is determined in a biological sample of the patient, said marker being selected from a) the amino acid sequence SEQ ID No. 2 from the sequence protocol that is provided, or b) a nucleic acid that encodes the amino acid sequence with the SEQ ID No. 2. The invention further relates to the amino acid and the encoding nucleic acid and to the use thereof in diagnostics and for molecular therapeutic approaches.

16 Claims, 5 Drawing Sheets

P53 BSt = p53 binding site

SEQ ID NO: 9

SEQ ID NO: 10

ASPP2 SPLICING VARIANT

CROSSREFERENCES TO RELATED APPLICATIONS

This application is a continuation of international patent application PCT/EP2011/063283, filed on Aug. 2, 2011, designating the U.S., which international patent application has been published in German language and claims priority from German patent application DE 10 201 0 033 575.4, filed on Aug. 2, 2010. The entire contents of these priority applications are incorporated herein by reference.

BACKGROUND OF THE INVENTION

The present invention relates to a novel ASPP2 splicing variant, more particularly a nucleic acid sequence and an amino acid sequence derived therefrom, for use as a marker for diagnosing cancer.

In general, the term "cancer" covers both solid tumors and malignant hemoblastoses. Since cancer is the second most common cause of death after diseases of the cardiovascular system in most industrial countries, the diagnosis and treatment of cancer is of very high medical, economical and also social and sociopolitical importance.

Cancers have a varied and often multifactorial etiology. They can affect all organs of the human body or arise from the corresponding tissues. Consequently, cancers are very heterogeneous even at the cellular level, and this often makes diagnosis thereof difficult.

With regard to tissue morphology, cancers are differentiated between solid tumors and, as in the case of hemoblastoses, individual cells which are separated from one another.

One of the most common hemoblastoses is acute myeloid leukemia. This is a disease of the hematopoietic system which leads to a strong increase in immature blood-cell precursors in bone marrow and, frequently, also in blood.

Whereas the treatment of solid tumors is therapied in the vast majority of cases by means of surgical removal in combination with radiation therapy, hemoblastoses such as acute myeloid leukemia are treated by chemotherapy, possibly supported by bone marrow transplantation.

A known problem in the chemotherapy of acute myeloid leukemia is the response to the chemotherapy, which is sometimes very diverse. For instance, for a particular proportion of patients, increased therapy refractoriness with respect to chemotherapeutics can be observed. This is associated with a distinctly worsened chance of recovery.

A further problem, which equally affects cancer types involving solid tumors and hemoblastoses, is the problem of minimal residual diseases. In the case of therapy in terms of surgical removal, radiation therapy or chemotherapy, individual cancer cells may remain in the body of the patient and possibly, after a certain latency time, lead to a recurrence of cancer. Since such minimal residual diseases nullify the success of therapy as a whole, considerable attention is also paid to their identification in cancer diagnostics.

Such diagnostics are based, as is also the case for general cancer diagnostics, mostly on DNA- or RNA-determining assays which make it possible to detect genetic aberrations characteristic of cancer cells or of the development of cancer. In addition, immunological tests which make it possible to detect cancer cell-specific markers on the cell surface or in the cytoplasm are also used. Other methods applied in cancer diagnostics are based on the detection of aberrant transcription profiles of cancer cells in relation to healthy cells of the tissue of origin.

Such diagnostic methods can lead to specific therapy if the altered transcription profiles provide information about the etiology or genetics of the particular cancer.

In the context of such diagnostic analysis, various markers are measured with regard to their presence or nonpresence or their intracellular concentration. In cancer diagnostics, both nucleic acid and amino acid sequences are used as markers, which can be detected by means of appropriate methods. At the genetic level, the markers can be detected by specific amplification and/or binding of labeled probes, whereas at the protein level, detection is achieved, for example, by means of antibodies which bind specifically.

For example, US2002/0086384 A1 describes a range of transcripts and proteins which arise as a result of alternative splicing and which can be used as markers in the context of cancer diagnostics.

However, many of the known markers, seen individually, do not make reliable diagnosis possible. There is therefore a need for additional, reliable markers for the definite diagnosis of cancer.

SUMMARY OF THE INVENTION

Against this background, it is an object of the present invention to provide markers which allow reliable identification of cancer and which, furthermore, allow further data to be obtained, if possible, about the transcription profile of the affected cells, said data being useful for the treatment of the particular cancer.

This object and other objects are achieved according to the invention by a method for the in vitro determination of the presence of cancer or of a predisposition of a patient to the development of cancer, wherein the presence of a marker selected from a) an amino acid comprising the amino acid sequence SEQ ID No. 2 from the attached sequence listing, or b) a nucleic acid comprising a nucleic acid encoding the amino acid sequence having SEQ ID No. 2 is determined in a biological sample from the patient.

Sequence Listing

The Sequence Listing is submitted as an ASCII text file [7291-90551-01_Sequence_Listing.txt, May 1, 2014, 13.7 KB], which is incorporated by reference herein.

According to an embodiment of the invention, the marker is an ASPP2 isoform which, compared to the naturally occurring ASPP2 isoforms, is shortened in the C-terminal region and which contains the amino acid sequence having SEQ ID No. 2, and according to another embodiment, the marker is selected from a) the amino acid sequence having SEQ ID No. 2;

b) a nucleic acid encoding the amino acid sequence having SEQ ID No 2.

The cancer which can be diagnosed or predicted by means of the method according to the invention is selected from hematologic neoplasias, more particularly leukemias (such as acute myeloid and lymphoblastic leukemia and chronic myeloid leukemia), solid tumors and precancerous conditions.

Accordingly, the invention also provides an amino acid sequence comprising or consisting of the amino acid sequence reproduced by SEQ ID No. 2 for use as a marker for the diagnosis of cancer or for the prediction of the development of cancer.

In this regard, ASPP2 stands for "apoptosis-stimulating protein of p53" and is also referred to as TP53BP2 (tumor protein p53 binding protein, 2) or 53BP2, BBP, P53BP2 or PPP1R13A (NCBI Genbank GeneID 7159). Via direct binding of p53, ASPP2 triggers or intensifies the induction of programmed cell-death mechanisms, i.e., apoptosis, following cell stress. Firstly, according to findings from the inventors, increased tumor therapy refractoriness is associated therewith. Furthermore, in a mouse model, lowered ASPP2 expression leads to increased tumor incidence owing to the absent capacity for regulated apoptosis induction following cell damage. In line with this, ASPP2 suppression has been documented in many human cancer types. Accordingly, low expression of ASPP2 has been correlated with increased tumor incidence, a poorer chance of survival and a poorer response to therapies.

The inventors have now identified, in about 50% of the patients who were examined by them and have acute myeloid leukemia, a previously unknown splicing variant of the tumor suppressor gene ASPP2, hereinafter referred to as ASPP2 transcript variant κ. This encodes an ASPP2 protein variant, hereinafter referred to as ASPP2 isoform κ, in which, compared to the known ASPP2 protein variants, large parts of the C-terminus containing the p53 binding sites are deleted. Consequently, ASPP2 isoform κ has lost the ability to induce apoptosis via p53 following cell stress/damage.

Initial additional results show that both ASPP2 transcript variant κ and ASPP2 isoform κ also occur in other forms of leukemia, lymphomas and solid tumors.

According to findings from the inventors, the transcript variant can have been generated both at the RNA level, i.e., by alternative splicing, or else can already be manifested in the genome of the individual affected, i.e., the information for the transcript variant is already genetically defined in the DNA of the individual affected. Therefore, according to the invention, detection of the marker can also take place at the DNA level, in which detection the nucleic acid sequences encoding the marker are detected in the genetic information of the individual to be examined.

According to findings from the inventors, the genomic sequence, the transcripts and translation products of this novel splicing variant are thereby outstandingly suitable as markers for cancer diagnostics. Consequently, by detecting said markers, it is possible to identify patients and patient groups having an increased malignancy risk and to generate statements about mortality and response to therapy. Furthermore, said markers are ideally suited to therapy monitoring.

Accordingly, according to the invention, a nucleic acid encoding the amino acid sequence having SEQ ID No. 2 is understood to mean, inter alia, mRNA, cDNA or the mRNA-encoding nucleic acid (gDNA).

Since the ASPP2 transcript variant κ according to the invention, i.e., the protein translated therefrom, cannot induce apoptosis via p53, the patients positively tested for the novel markers are susceptible to increased therapy refractoriness with respect to cytostatic/cytotoxic therapeutics. Therefore, for this patient group, specific therapies for driving tumor cells into programmed cell death by restoring "normal" ASPP2 activity and/or for (re)improving sensitivity with respect to other therapeutics are appropriate.

In this regard, the restoration of ASPP2 wild-type expression by stimulation of transcription, for example by means of demethylating substances or by means of gene transfer or supplementation of wild-type ASPP2, can be just as meaningful as the simulation of the ASPP2 wild-type function by antibodies or small molecules which are administered to the patient and which activate the ASPP2 binding sites on p53 or mimic the ASPP2 p53 binding sites. Thus, according to the invention, the present invention also provides for the use of such means for restoring ASPP2 wild-type expression.

Thus, the novel markers provide not only pure diagnostics but also advantages in the context of improved therapy, which can be aligned with the diagnostics.

The particular diagnostic and therapeutic relevance of the novel markers can be explained as follows, without the inventors wishing to be restricted to this explanation.

ASPP2 belongs to the family of the ASPP proteins, which were first described in 1994; Iwabushi, K. et al. (1994): Two proteins that bind to wild-type but not mutant p53 *Proc. Natl. Acad. Sci. USA* 91: 6098-6102. In mammals, three members of the ASPP family are known altogether: ASPP1, ASPP2 and the most evolutionarily conserved iASPP. All three proteins have high sequence homology in the region of their C-terminus, in which primarily binding sites for ASPP binding partners, for example the protein p53 and bcl-2, are present; Gorina, S and Pavelitch, NP (1996): Structure of the p53 Tumor Suppressor bound to the anchyrin and SH3 domains of 53BP2. Science 274: 1001-1005; Naumovski, L and Cleary, ML (1996): The p53 binding protein 53BP2 also interacts with bcl2 and impedes cell cycle progression at G2/M. *Mol. Cell. Biol.* 16: 3884-3892.

The best characterized function so far of the ASPP protein family relates to their ability to regulate p53-induced apoptosis. In this connection, ASPP2 intensifies the ability of p53 to specifically stimulate the expression of proapoptotic target genes; Samuels-Lev, Yet al. (2001): ASPP proteins specifically stimulate the apoptotic function of p53. *Mol. Cell.* 8: 781-794; Bergamaschi, D et al. (2004) ASPPI and ASPP2: Common Activators of p53 Family Members. *Mol. Cell. Biol.* 24: 1341-1350.

In contrast, the iASPP protein appears to carry out a function which is inhibitory to the function of ASPPI and/or ASPP2, by competitively binding the ASPP binding sites on, for example, p53 and thus inhibiting the function of ASPPI and ASPP2; Bergamaschi, D et al. (2003): iASPP oncoprotein is a key inhibitor of p53 conserved from worm to human. *Nat. Genet.* 33: 162-167.

In this regard, a series of experimental results indicates that the haploid tumor suppressor ASPP2 plays an important role in the regulation network of p53-induced apoptosis, and in a range of relevant cancers, reduced expression of ASPP2 can also be detected. For instance, it has been shown that ASPP2 heterozygous mice have a distinctly increased occurrence, compared to homozygous wild-type mice, of tumors over their lifespan; Kampa K M et al. (2009): Apoptosis stimulating protein of p53 (ASPP2) heterozygous mice are tumor-prone and have attenuated cellular damage-response thresholds. *Proc. Natl. Acad. Sci. USA* 106(11): 4390-4395; Vives Vet al. (2006): ASPP2 is a haploinsufficient tumor suppressor that cooperates with p53 to suppress tumor growth. *Genes and Development* 20: 1262-1267.

Proceeding from the ASPP2 gene, which comprises 19 exons altogether, various transcripts are produced by alternative splicing. The database (Genbank) of the National Center for Biotechnology Information (NCBI) stores two transcripts of the ASPP2 gene, ASPP2 transcript variant 1 (database No. NM_001031685) and ASPP2 transcript variant 2 (database No. NM_005426). The numbering of the exons corresponds hereinbelow to the numbering according to the abovementioned Genbank entries with respect to ASPP2 transcript variants 1 and 2.

ASPP2 transcript variant 2 comprises all the exons, 1 to 19, of the ASPP2 gene and has a length of 3405 bp (according to the NCBI Consensus CDS [CCDS] Project, CCDS ID: CCDS44319.1). In contrast, in the case of ASPP2 transcript variant 1, exon 3 is removed by splicing, producing a shortened sequence, with respect to transcript variant 2, of 3018 bp altogether (CCDS ID: CCDS1538.1).

Both transcripts encode isoforms of the ASPP2 protein: transcript variant 1 for isoform 1 and transcript variant 2 for isoform 2.

ASPP2 isoform 1 (database No. NP_001026855) is, at 1134 amino acids (aa), the larger of the two proteins. ASPP2 isoform 2 (database No. NP_005417) is, despite the integration of exon 3 into transcript variant 2, an N-terminally truncated isoform (having an alternative start codon situated further C-terminally compared to isoform 1) of 1005 aa in length, which, however, is otherwise identical in sequence to isoform 1.

As already mentioned further above, the C-terminal region contains the binding domains required for binding to known binding partners, for example p53 or bcl-2.

Both known isoforms are, fundamentally, expressed in both healthy tissue and tumor tissue. In particular diseases, repression of the ASPP2 gene may be present in the cancer cells.

As already mentioned, the inventors of the present application have now found in their own investigations that, surprisingly, a further transcript variant which is detectably expressed in tumor tissues exists in addition to the known transcript variants.

As shown in FIG. 1, said transcript variant arises by misssplicing with the omission of the whole of exon 17. Owing to said missplicing, transcription of exon 18 follows directly after exon 16. This results in a reading frame shift with a distinctly shortened transcript having a sequence characteristic of this variant (see FIG. 6A; and Seq. ID No. 1 and 2 from the attached sequence listing).

Said reading frame shift, in turn, causes the protein which is encoded by the transcript in question and is subsequently referred to as ASPP2κ (kappa) to have a modified C-terminus with respect to the ASPP2 wild type. In keeping with the N-terminally differentially encoded transcription variants ASPP2 isoform 1 and isoform 2, corresponding isoforms for ASPP2κ (ASPP2κ isoform 1 and ASPP2κ isoform 2) are also to be found. Furthermore, according to findings from the inventors, there is also at least one further N-terminally truncated ASPP2κ isoform.

As already mentioned, ASPP2κ has a sequence of 9 amino acids in length that is unique to the ASPP2 isoform κ protein (Seq. ID No. 2 from the accompanying sequence listing) and is, furthermore, greatly shortened with respect to the known protein variants. This shortening, and also the reading frame shift, affects in particular the abovementioned part of the known ASPP2 isoforms in which the binding sites for the binding of the ASPP2 proteins to, for example, p53 or bcl-2 are located, as shown in FIG. 2.

Consequently, ASPP2 isoform κ is a protein which, in contrast to the ASPP2 isoforms 1 and 2 also occurring in healthy tissue, cannot develop any binding activity with respect to p53.

With the formation of the ASPP2 transcript variant κ as part of an alternative splicing process, the formation of the functionally intact ASPP2 isoforms 1 and 2 is completely or at least largely lost in the tumor cells, and this is associated with missing or at least greatly reduced activity of the ASPP2 protein in tumor cells. In other words, in the tumor cells, there is no apoptosis induction, or only inadequate apoptosis induction, via the p53 signal transduction pathway.

Apoptosis induction, however, is an important basis for the (a) maintenance of cell and tissue integrity following cell stress, and (b) for the control of cancer by means of chemotherapeutics.

During cell division (mitosis), instances of faulty replication constantly occur, and these can be reliably rectified in the vast majority of cases by various repair mechanisms. Particularly after cell stress, for example chemicals (e.g., benzenes) or radioactive or UV radiation, the number of replication errors increases, and there is the risk of repair mechanisms failing and of faulty nucleic acid sequences being passed on to the daughter cell(s)—depending on the gene affected, this can signify a first step in oncogenesis. Self-destruction by means of induction of programmed cell death (apoptosis) is used by the cell as the last mechanism within the repair machinery in order to protect the surrounding tissue and, ultimately, the entire organism. A faulty p53/ASPP2 interaction prevents this, with the result that faulty (mutagenic) nucleic acid sequences can be transmitted into the daughter cells during mitosis.

Despite different approaches, mostly in the region of the cell-division machinery, what chemotherapeutics have in common is that programmed cell death (apoptosis) is initiated resulting from induced cell damage. The p53/ASPP2 interaction plays a significant role here and ASPP2 functionality is thus a codeterminant for the efficiency of chemotherapy.

ASPP2κ can thus be understood to be a precancerous condition or early aberration in the context of tumorigenesis.

Moreover, in the case of ASPP2κ-positive cancers, increased therapy refractoriness has to be assumed.

Consequently, the newly discovered transcript and protein variants of ASPP2 allow a completely new type of cancer diagnostics.

Although U.S. Pat. No. 5,977,311 describes protein complexes comprising an ASPP2 protein, and also diagnostic methods and treatment methods based on said protein complexes, the known diagnostics are restricted to the known isoforms of the ASPP2 protein to be found in every body tissue.

The same applies to U.S. Pat. No. 7,081,340, which relates to a method for diagnosing cancer, in which the concentration of a range of transcripts, including ASPP2, in a biological sample is determined. Here, too, there is no indication of the aberrant splicing variant described by the inventors of the present invention.

In contrast, the ASPP2 transcript and protein variants described by the inventors of the present application allow simple, specific differentiation not only between tumor and normal tissue, but also between tumor tissues of different functional properties.

Thus, the diagnostic recording and quantification of ASPP2κ gene products within a cell population provides not only information for cancer diagnosis per se, but also important information for the therapy and prognosis of a particular cancer.

According to the invention, it is also possible to use as marker an amino acid which is joined N-terminally as fusion site to the amino acid sequence SEQ ID No. 2, or a nucleic acid comprising a nucleic acid comprising the N-terminally situated fusion site of the amino acid sequence having SEQ ID No. 2.

Said "fusion site" is, in each case, the amino acid sequence read from the transcript variant in which exon 17 is missing and in which, as a result, the sequence of exon 18 is read directly after the sequence of exon 16. Therefore, the marker according to the invention also encompasses amino acid sequences which are joined to such fusion sites.

It will be appreciated that the novel method for diagnosing cancer can be used not only for patients already suffering from cancer, but also for healthy individuals or those suffering from another condition. In this way, it is possible to obtain information about the particular cancer risk of a patient and about therapeutic approaches required in the case of a subsequent cancer. More particularly, the method can also be used for the diagnosis of/in the case of diseases potentially promoting cancer.

The object underlying the present invention is completely achieved in this manner.

In the context of the present application, an "amino acid sequence" is understood to mean a sequence constructed of two or more amino acids, wherein the amino acids originate from the group of the twenty naturally occurring amino acids and of the derivatives obtained therefrom by chemical modification. The amino acid sequence has a primary structure, i.e., the sequential succession of amino acids, and can form secondary structures, for example an α-helix or β-sheet, and tertiary structures, for example in a correctly or aberrantly folded protein.

In this regard, an amino acid sequence identical according to primary structure can be encoded by nucleic acid sequences having different sequences. This is caused by codon degeneracy, which results in different codons (i.e., nucleic acid triplets) encoding the same amino acid.

In the present context, a deleted binding site is understood to mean a binding site which has lost its ability to bind, completely or at least partially, owing to partial or complete deletion. In this case, such a deletion can be caused by a deletion or a reading frame shift of the nucleic acid sequence underlying the amino acid sequence. Such a reading frame shift causes altered coding, with respect to the nonshifted reading frame, of the nucleic acid sequence in question, generating an altered amino acid sequence at this site during the translation of the nucleic acid sequence.

In the context of the present application, "nucleic acid sequence" is understood to mean in particular a macromolecule which is constructed as a sequence of deoxyribonucleic acid (DNA) nucleotides or ribonucleic acid (RNA) nucleotides. The nucleic acids to be determined can be present in the sample both as single strands and as double strands. The term includes in particular—but is not restricted thereto—DNAs and RNAs, more particularly mRNAs, microRNAs, rRNA and noncoding RNAs and also cDNAs generated therefrom by reverse transcription, and also genomic DNA (single-stranded and double-stranded), and synthetic or modified nucleic acids. Moreover, the term "nucleic acid" also encompasses aptamer DNA and RNA and fragments of genomic DNA which can in particular also be methylated.

Said nucleotides can also have a range of chemical modifications. However, in the present context, the term "nucleic acid sequence" also encompasses, besides said naturally occurring sequences, sequences which are constructed from nucleotide analogs obtained by chemical synthesis or combinations with the aforementioned nucleotide types.

Examples of nucleotide analogs are peptide nucleotides, L-nucleic acids or morpholinos. Corresponding synthesis methods for monomers or polymers are known from the prior art.

A nucleic acid sequence is firstly determined by its primary structure, i.e., by the sequential succession of nucleotides within the polymer, but it can also form structures of higher order which arise owing to the physical or physicochemical interaction of particular regions or nucleotides within the sequence or between separate sequences. Examples of such higher structures are hairpin loops or double strands.

According to an embodiment of the invention, the method according to the invention comprises the following steps: a) providing a biological sample, b) contacting the biological sample with at least one binding reagent which specifically binds a marker according to the invention, c) detecting at least one marker according to the invention contained in the biological sample, and d) quantifying the at least one marker from step c).

In this connection, and according to another embodiment, one or more steps for isolating, purifying, concentrating and/or chromatographically separating nucleic acid sequences or amino acid sequences can be provided between steps a) and b).

Using the method according to the invention, the detection of the ASPP2κ marker can be performed directly in appropriately obtained tissue or cell samples. Appropriate methods, for example the in situ hybridization of nucleic acid probes to transcripts present in the tissue or cell samples or the antibody staining of proteins, are comprehensively known to a person skilled in the art. The detection can also be carried out via PCR methods known per se, in which the binding reagents according to the invention are used as probes and/or primers.

Such methods make it possible to establish whether corresponding transcripts or proteins specifically detected by the nucleic acid probe or the antibody are present in the tissue or cell samples, and allow, beyond this qualitative statement, possibly a semiquantitative analysis, in which the degree of expression or translation of the markers in question is correlated with other markers.

Said other markers can be, for example, other gene products of ASPP2 or of housekeeping genes, the mRNA or protein concentration of which in the tissues or cells examined is known.

Further methods which allow a possibly more precise quantitative analysis of an expression pattern or of protein concentrations are Northern or Western blotting or the use of DNA or protein microarrays. Such methods and devices are known from the prior art.

The method according to the invention thus allows not only a qualitative statement with regard to whether ASPP2κ markers are even contained in the tissue or cell samples, but also allows a semiquantitative or even quantitative analysis of ASPP2κ transcription and/or translation in the samples in question.

In this regard, it is also possible to use the information obtained via the diagnostic method according to the invention in order to specifically counteract therapy refractoriness in individual cancers.

In the case of a reduction in ASPP2 function based solely on the dysfunctionality of the isoform κ, this can be achieved by supplementation of the corresponding transcript variants 1 and 2 and, possibly, of the corresponding proteins isoform 1 and 2. In addition, it is of course also possible to perform stable supplementation by means of gene therapy, i.e., by local or systemic infection of the patient with a virus carrying an ASPP2 gene variant not susceptible to incorrect splicing.

Besides the method for the in vitro diagnosis of cancer, the present invention provides an isolated amino acid sequence which corresponds to a naturally occurring ASPP2 isoform having a truncated C-terminus and the p53 binding sites located therein, and which comprises the sequence having SEQ ID No. 2. More particularly, the present invention provides an isolated amino acid sequence, resulting from a frame shift of the original (wild-type) amino acid sequence, having exon 17 splicing. This translation variant bears a characteristic 9 amino acid long sequence at the C-terminal end and is, as already mentioned further above, greatly shortened compared to the wild type.

The amino acid sequence according to Seq. ID No. 2 corresponds to the 9 amino acid long sequence specific to ASPP2κ isoforms, which sequence arises by translation of the shifted reading frame in ASPP2 transcript variant κ and is located at the C-terminus of ASPP2 isoform κ.

The amino acid sequence having SEQ ID No. 1 shows the complete amino acid sequence of an ASPP2κ isoform identified by the inventors, which is altogether 879 amino acids in length and has a total molecular weight of about 97 kDa.

SEQ ID No. 3 shows the mRNA of said ASPP2κ isoform, wherein bases No. 3422 to 3448 encode the sequence specific to the isoform. Therefore, the invention also provides for the detection of a nucleic acid sequence which encodes the amino acid sequence having SEQ ID No. 1 or 2, i.e., more particularly the mRNA which encodes the isoform and which is shown in SEQ ID No. 3, or the segment of said mRNA which encodes the specific sequence, i.e., bases No. 3422 to 3448, or a genomic sequence which encodes the mRNA nucleic acid sequence or the segment, and also a sequence which comprises sequences which are directly joined to SEQ ID No. 2.

In the context of the present application, the term "isolated" means that the substance in question is not located in the context of its natural place, i.e., within the human body.

The amino acid sequence according to the invention can include the complete ASPP2κ isoform on its own or, for example, as part of a fusion protein. However, it is preferred when it comprises in particular only the sequence specific to ASPP2κ.

As part of a method for diagnosing cancer, such an amino acid sequence can be isolated along with a biological sample and used as a marker.

Furthermore, an amino acid sequence according to the invention can also be used for the generation or identification of specific binding reagents which are used in such a method or in the context of treatment.

For this purpose, the amino acid sequence can be produced by known methods, i.e., by expression of a vector in a microorganism, by in vitro translation or by chemical synthesis. In this regard, a microorganism is to be understood to mean in particular a bacterium or a eukaryotic cell, for example an isolated, immortalized mammalian cell, a yeast cell or a filamentous fungus.

As mentioned, a thus produced amino acid sequence comprising the sequence specific to ASPP2κ isoforms can be used for the generation or identification of specific binding reagents or detection molecules. For this purpose, a nonhuman organism, preferably a mammal, is immunized against the amino acid sequence for example. Subsequently, antibodies which specifically bind the amino acid sequence, or cells expressing such antibodies, can be obtained by means of known techniques. Alternatively, the ASPP2κ isoform-specific sequence can also be used to screen for other binding reagents, for example other proteins or small molecules.

In this regard, small molecules are to be understood to mean a heterogeneous group of small organic molecules of a size usually below 800 Daltons (Da), for example secondary metabolites or synthetically produced variations thereof.

In addition, the present invention also provides a corresponding isolated nucleic acid sequence selected from the group comprising a) a nucleic acid sequence encoding an amino acid sequence according to the invention having Seq. ID No. 1 or 2, b) a nucleic acid sequence comprising a sequence having at least 90% sequence identity with the sequence having SEQ ID No. 3, c) a nucleic acid sequence which at least partly encodes the amino acid sequence having SEQ ID No. 2, i.e., at least 3 of the amino acids, and also a region of at least 2 amino acids which is joined N-terminally thereto in each case, and d) a nucleic acid sequence which is complementary or reverse complementary to a), b) or c).

The nucleic acid sequence according to Seq. ID No. 3 is the already mentioned sequence of ASPP2 transcript variant κ, which comes about as a result of the transition between ASPP2 exon 16 and ASPP2 exon 17 that arises in the course of the faulty splicing process.

In this regard, in the context of the present application, the term "complementary" or "reverse complementary" is understood to mean the ability of a nucleic acid sequence to bind physically or physicochemically to another nucleic acid sequence with continuous formation of canonical nucleotide base pairs such as AU, AT and GC. Such binding is achieved, for example, between the individual strands of a double-stranded DNA and, during transcription, between a DNA strand acting as a template and a newly formed RNA strand, and, during translation, between a particular region of a messenger RNA and a particular region of a transfer RNA.

Such a nucleic acid sequence can, just like an abovementioned amino acid sequence, be isolated along with a biological sample and used as a marker in the context of a method for diagnosing cancer.

A nucleic acid sequence according to the invention can also be used for preparing an amino acid sequence having the above-described properties in a sufficient amount, thereby making it possible to develop, prepare and test detection methods and/or detection molecules, for example antibodies, for the markers.

Furthermore, such a nucleic acid sequence can also be used directly as a detection molecule, for example as part of a diagnostic method. These detection molecules include binding reagents such as, for example, nucleic acid primers and probes for the detection of ASPP2 transcript variant κ.

Furthermore, a nucleic acid sequence according to the invention, or the deleted wild-type sequence, can also be used either directly or as part of a vector as active ingredient in the context of treatment.

For this purpose, such a nucleic acid sequence can, for example, be amplified by known methods such as PCR or transcribed by expression of a suitable gene construct and, for example, be used in a manner known per se to generate other gene constructs, to generate transcripts, specific nucleic acid probes and primers or proteins.

In the context of the present application, "transcription" is understood to mean the formation of a ribonucleic acid sequence (RNA) on the basis of a deoxyribonucleic acid sequence (DNA), whereas "reverse transcription" is understood to mean the formation of a deoxyribonucleic acid sequence on the basis of a ribonucleic acid sequence.

In this regard, nucleic acid probes and primers are to be understood to mean in particular single-stranded DNA or RNA sequences of short to medium length (about 10 b up to several 100 b) which can hybridize under stringent conditions to complementary DNA or RNA sequences. Appropriate hybridization conditions are comprehensively known to a person skilled in the art, for example in conjunction with techniques such as polymerase chain reaction, Southern or Northern blotting.

Since various organisms, for example model organisms or organisms for the biotechnological preparation of amino acid sequences or proteins, often exhibit codon preferences which deviate from humans, it may be necessary in the course of the biotechnological production of an amino acid sequence to modify a nucleic acid sequence by replacing particular codons with other codons encoding the same amino acid. As a result, it is frequently possible to achieve improved expression or a lowering of the error rate during expression.

In this regard, the present invention further provides a vector comprising a nucleic acid sequence according to the invention.

In this regard, a "vector" describes a genetic or organismic context into which a nucleic acid sequence is structurally and/or functionally integrated. For example, a vector can be understood to mean a naturally occurring or synthetically produced plasmid, a naturally occurring or synthetically produced chromosome or another nucleic acid sequence which, besides the possibility of inserting a further nucleic acid sequence thereinto via a synthetic or natural route, comprises sequences or genes required for the replication and/or expression of said additional nucleic acid sequence. Such plasmids and chromosomes are comprehensively known to a person skilled in the art.

Furthermore, a vector can also be understood to mean an organism, preferably a virus, which is able to infiltrate eukaryotic tissue and via which a nucleic acid sequence can be administered to eukaryotic cells. Such vectors are comprehensively known from the prior art to a person skilled in the art.

In the context of the present invention, a vector can contain an ASPP2κ-specific sequence composition which, for example, is integrated into the context of a complete open reading frame (ORF) encoding ASPP2κ isoforms. Furthermore, the ASPP2κ-specific sequence composition can be integrated into an ORF encoding a fusion protein. Furthermore, it is also possible to produce RNA-interference constructs in a known manner using the ASPP2κ-specific sequence composition. This is done, for example, by generating a palindromic sequence or a hairpin loop which makes it possible to produce a double-stranded RNA having an ASPP2κ-specific sequence composition.

Furthermore, the present invention provides a binding reagent which binds specifically to a nucleic acid sequence according to the invention or to an amino acid sequence according to the invention. In this case, it is particularly preferred when the binding reagent is selected from the group comprising a) nucleic acid probes and primers, b) antibodies, including antibody derivatives, and c) small molecules.

In this regard, "antibody derivatives" are to be understood to mean an antibody-derived structure, for example an antibody fragment or a chimeric antibody. A special form of the chimeric antibody is the humanized antibody which is expressed in murine cells for example and in which all sequence parts not directly involved in the specific binding to the antigen have been replaced with human antibody sequences. Thus, an immune response of the human body toward the nonspecific antibody parts can be prevented or modified.

Such a binding reagent specific for ASPP2 transcript variant κ or ASPP2κ isoforms can be used as part of diagnostics in order to bind ASPP2 transcript variant κ or the ASPP2κ isoforms in biological samples from the human or animal body and to thus allow direct or indirect detection thereof.

For this purpose, the binding reagent can be configured for direct detection, by comprising, for example, a fluorophore, a catalyst, a radioactive isotope, a magnetic particle or other detectable materials or properties. Alternatively, such detectable materials or properties can also be provided on secondary binding reagents, for example secondary antibodies, which specifically bind the first binding reagent. Such detection materials, secondary binding reagents and methods are known comprehensively from the prior art to a person skilled in the art.

Accordingly, the present invention also provides a diagnostic kit which comprises one or more reagents from the group comprising a) an amino acid sequence according to the invention, b) a nucleic acid sequence according to the invention, c) a vector according to the invention and d) a binding reagent according to the invention. Furthermore, in a preferred embodiment, the diagnostic kit comprises a microarray.

Such a diagnostic kit can be used for the above-described method and thus allows the detection of an ASPP2κ marker for the purposes of qualitative and, possibly, quantitative analysis. In this case, particularly in the case of a microarray, a multiplicity of known gene products of oncogenes or proto-oncogenes and also other markers (see above) can be measured in parallel in a quantitative or semiquantitative manner.

Such an analysis thus allows a further differentiated statement about the probable progression of a particular cancer or about the ability thereof to be therapied.

Accordingly, the present invention also provides a pharmaceutical composition which comprises one or more active ingredients from the group comprising a) an amino acid sequence according to the invention, b) a nucleic acid sequence according to the invention, c) a wild-type nucleic acid sequence, d) a vector according to the invention and e) a binding reagent according to the invention. The pharmaceutical composition can further comprise synthetic so-called small molecules having mimicry of the lost P53 binding sites, and also cellular and antibody-based immunotherapeutics. In the present context, "small molecules" are understood to mean any low-molecular-weight compound or active ingredient, the molecular mass of which does not exceed about 800 $g \cdot mol^{-1}$ and which, owing to the small size, is capable of entering cells and of developing its action there.

A pharmaceutical composition can, in addition to one or more active ingredients, also comprise a range of excipients and/or auxiliaries which, for example, allow a longer shelf life or more effective administration. Such excipients and auxiliaries are known comprehensively from the prior art; cf. Row et al. (2006), Handbook of Pharmaceutical Excipients, 5th edition, Pharmaceutical Press; or Bauer et al. (1999), Lehrbuch der Pharmazeutischen Technologie ("Textbook of Pharmaceutical Technology"), 6th edition, Wissenschaftliche Verlagsgesellschaft Stuttgart mbH. The content of the present publications is, by way of reference, part of the present application.

Such a pharmaceutical composition can, as explained above, be used for either the prevention or treatment of cancers. In this case, it is conceivable to support or even replace conventional treatment using surgical therapy, chemotherapy or radiation therapy by administration of a pharmaceutical composition according to the invention. In addition, a pharmaceutical composition according to the invention can also be used following conventional treatment for prevention against a recurrence of the cancer, for example by means of a minimal residual disease.

More particularly, a pharmaceutical composition according to the invention can be used to resensitize ASPP2κ-positive cancer cells, i.e., cells in which apoptosis induction via ASPP2 and p53 is disrupted, to apoptosis-inducing stimuli. Subsequently, these cells can be stimulated to undergo apoptosis either by means of intracellular stimuli, the immune system or by means of tumor therapeutics such as, inter alia, chemotherapy and radiation therapy. More particularly, patients in whom the ASPP2κ isoform according to the invention is present can be treated by the use of small molecules which mimic the p53 binding site, or by use and usage/supplementation of/with the wild-type sequence of ASPP2.

Consequently, the present invention also provides a method for treating a patient, wherein the method comprises the following steps: a) carrying out a method according to the invention for the in vitro diagnosis of cancer, b) administering a pharmaceutical composition according to the invention and c) repeating steps a) and/or b) if necessary.

The advantage of such a method is that one of the molecular causes of cancer, viz. ASPP2 insufficiency and the thus reduced induction of apoptosis, can be counteracted in a specific manner. The method according to the invention thus leads to a reduction in therapy refractoriness in the case of ASPP2κ-positive cancers.

The invention further provides a method for cellular immunotherapy for the treatment of cancer. According to the invention, cellular immunotherapy utilizes the fact that there is activation of cytotoxic T or NK (natural killer) cells which are directed or specifically oriented (by means of antibodies or antigen-presenting dendritic cells or hybrids) against (cancer) cells bearing the marker according to the invention, i.e., the specific, 9 amino acid long sequence or the N-terminally situated fusion site or parts thereof (also in complexes with other peptides/proteins, for example MHC complexes) which are contained in the ASPP2 transcript variants according to the invention. As a result, such "defects", the cells expressing transcript variants according to the invention, i.e., cancer cells, can be specifically attacked and neutralized. For example, the marker bearing the sequence according to the invention can be used as an antigen for activating the cytotoxic T cells.

Further advantages are evident from the attached description and the figures and tables.

It will be appreciated that the features mentioned above and the features yet to be explained below are usable not only in the particular specified combination, but also in other combinations or alone, without departing from the scope of the present invention.

BRIEF DESCRIPTION OF THE DRAWINGS

The gene locus of ASPP2, the known gene products and the gene products newly discovered at the applicant's site, the cellular mechanism of action of ASPP2, and the results of the experimental detection of ASPP2 transcript variant κ and of ASPP2κ isoforms in cancer cells of various tissue, as achieved at the applicant's site, are shown in the figures, in which.

DESCRIPTION OF PREFERRED EMBODIMENTS

EXAMPLE 1

ASPP2 Transcript Variants

Figure 1:
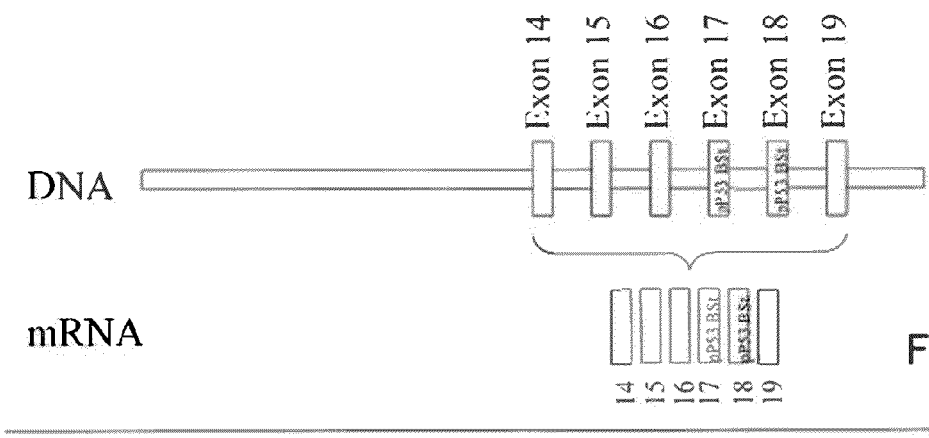
FIG. 1 shows a diagrammatic representation of the C-terminal end of ASPP2.

FIG. 1 shows a diagrammatic representation, not to scale, of a C-terminal region of the gene sequence encoding ASPP2 isoforms 1 and 2 (which are distinguished by differing splicing in the N-terminal region). What is shown is the nucleic acid sequence, along which the C-terminal exons 14 to 19 are arranged as white boxes. In the region of exon 17-18 (region of the 4th ankyrin repeat and of the SH3 domains) are located the p53 binding sites, which allow the binding of ASPP2 isoforms 1 and 2 to p53 proteins and thus a functional interaction. Said functional interaction leads to the induction of apoptosis.

Figure 2:
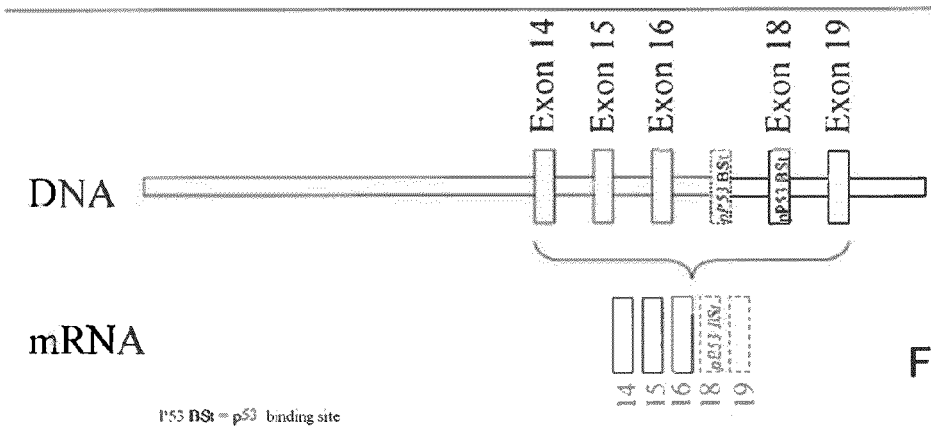
FIG. 2 shows a diagrammatic representation of the C-terminal end of ASPP2κ.

FIG. 2 shows, analogously to the scheme used in FIG. 1, a C-terminal region of the ASPP2κ isoforms. Compared to ASPP2 isoforms 1 and 2, ASPP2κ exhibits no transcription of exon 17 owing to alternative splicing, the cause of which is so far unexplained. As a result, all those p53 binding sites which are encoded by exon 17 are absent.

EXAMPLE 2

ASPP2 Translation Variants

Figure 3:
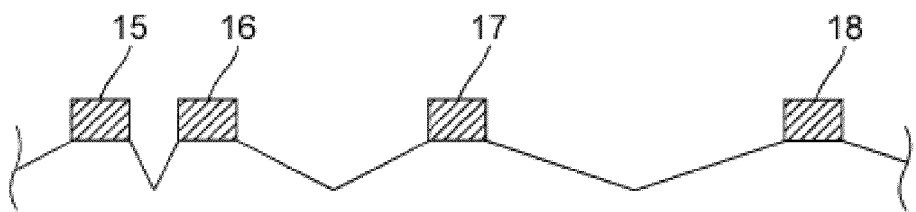
FIG. 3 shows a diagrammatic representation of ASPP2 transcript variants 1, 2.

FIG. 3 shows a diagrammatic representation, not to scale, of a segment from ASPP2 transcript variants 1 and 2. Here, exons (15, 16, 17, 18), i.e., the translationrelevant regions of the nucleic acid sequence, are depicted as rectangles, whereas the introns removed in the course of transcription by splicing are depicted by connecting lines between exons (15, 16, 17, 18). Here, the numbering of exons (15, 16, 17, 18) corresponds to the exon numbering according to the particular Genbank entries (database Nos. NM_001031685, NM_005426). The open reading frame (ORF) containing the information to be translated is depicted as a shaded area and completely fills exons (15, 16, 17, 18) shown here.

Figure 4:
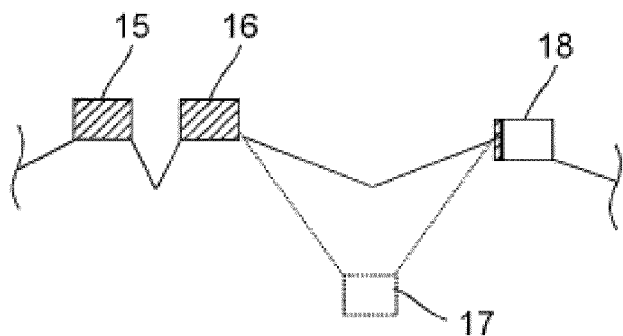
FIG. 4 shows a diagrammatic representation of ASPP2 transcript variant κ.

FIG. 4 shows, analogously to the scheme used in FIG. 3, the corresponding segment from ASPP2 transcript variant κ. In this variant, exon 17 has been completely deleted during transcription (FIG. 1). The reading frame shift which arises owing to the deletion of exon 17 leads to a characteristic 9 amino acid long sequence, novel for transcript variant κ, at the C-terminus (reproduced in Seq. ID No. 2): the frame shift leads to a shortened open reading frame having premature coding for a stop codon and thus to stopping of translation in exon 18. This is reflected in the shaded area in exon 18 which is represented diagrammatically in FIG. 4 and shorter compared to FIG. 3. As a result, the p53 binding sites encoded by exon 18 are no longer translated.

Thus, it is apparent that the p53 binding sites are completely deleted both by means of the reading frame shift-induced sequence change (example 2) and by means of the deletion of exon 17 (example 1) and have thus become dysfunctional. Binding of ASPP2 isoform κ can thus no longer be established by means of said p53 binding sites. As a result, the induction of apoptosis mediated by cooperation of ASPP2 and p53 is at least impaired.

EXAMPLE 3

Detection of ASPP2κ Gene Products in Leukemia Cells

Figure 5A:
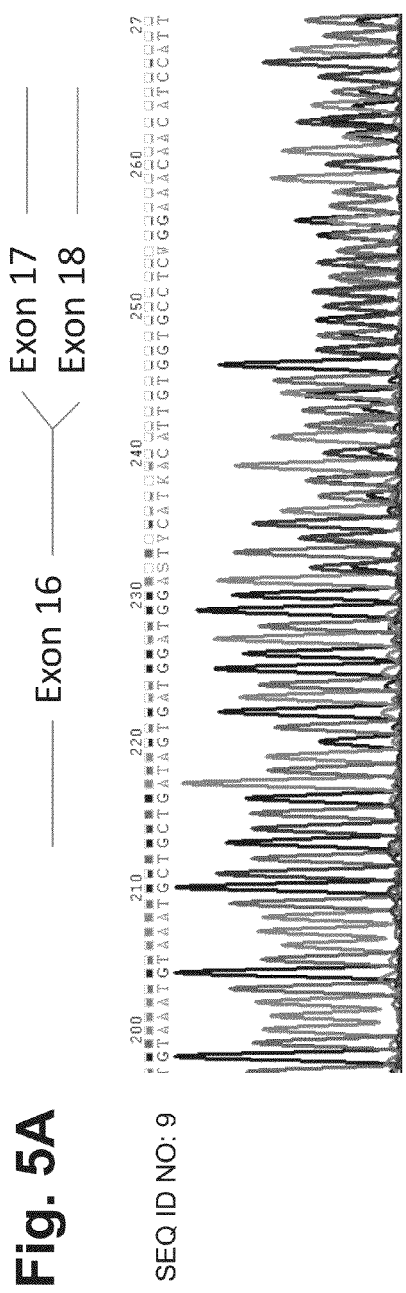
FIG. 5 shows the ASPP2 RNA of a patient suffering from acute leukemia and positive detection of ASPP2κ; (A) sense reading direction; (B) antisense sequence.
Figure 5B:
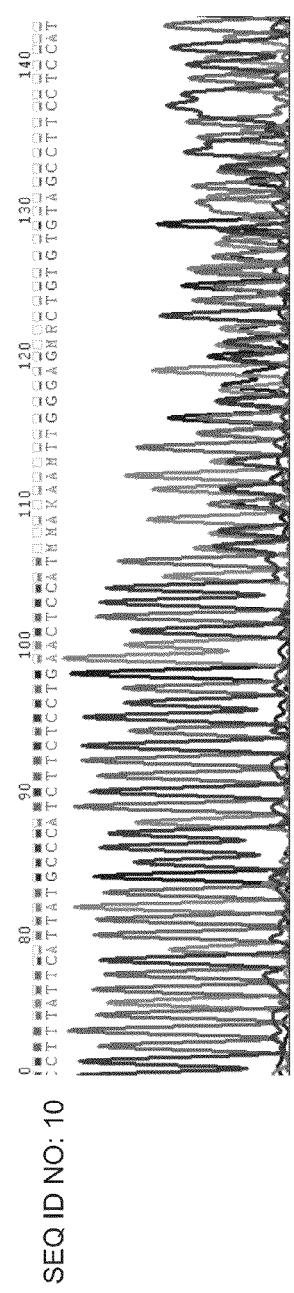

Mononuclear cells from a sample from a patient suffering from acute leukemia were isolated by means of density gradient centrifugation. mRNA was, in turn, isolated therefrom according to established protocols (Qiagen, Hilden, Germany) and reverse transcribed to form cDNA, which was analyzed by means of PCR and also directly sequenced. Accordingly, FIG. 5 shows the results of this sequencing:

FIG. 5A shows the ASPP2 DNA in the sense reading direction, FIG. 5B shows the antisense sequence.

As a result of the aberrant splicing of exon 17 in the ASPP2 κ transcript variant, both the ASPP2 wild-type sequence (i.e., including exon 17) and the shorter splicing variant having direct joining of exon 18 following exon 16 (i.e., with the omission of exon 17) are to be found. The sequence overlap indicates the simultaneous presence of two sequences: exon 17 and 18 in the sense direction (FIG. 5A), and exon 17 and 16 in the antisense direction (FIG. 5B).

In further experiments, it was shown that the expected ASPP2κ translation variant is actually also detectable at the protein level. For this purpose, specific polyclonal rabbit antibodies were generated using the 9 amino acid long sequence determined for ASPP2κ (for which a protein having the same partial sequence was not identified in a Blast database search).

Figure 6A:
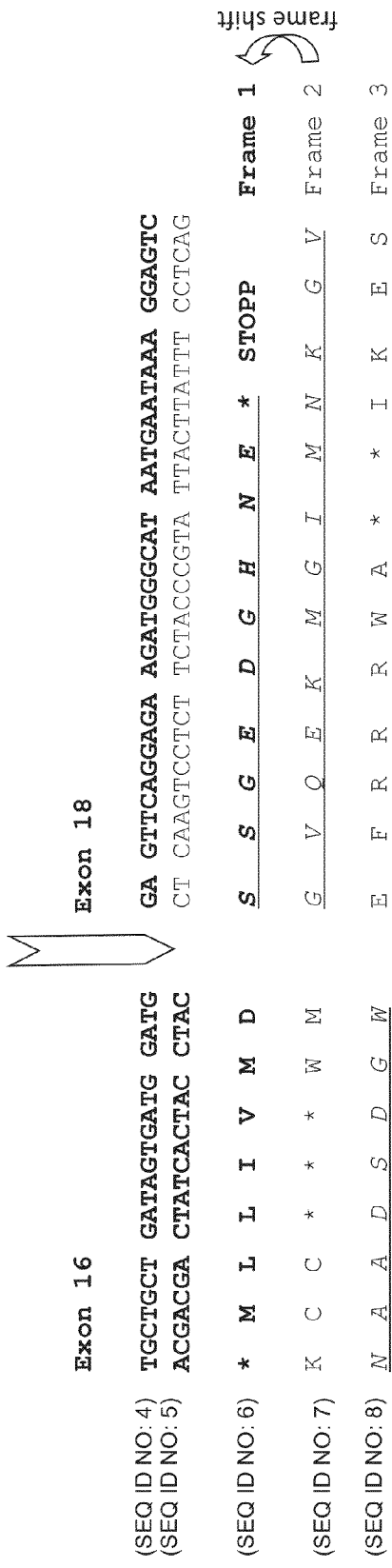
FIG. 6 shows an overview of the frame shift of ASPP2 transcript variant κ compared to the wild type (A) and Western blots showing the detection of ASPP2 transcript variant κ in patients suffering from acute leukemia (B).

FIG. 6A shows an overview of exons 16 and 18 of ASPP2, and how the frame shift came about in this region. Frame 2 shows the original wild-type sequence, and frame 1 shows the sequence for the ASPP2κ variant. The arrow in FIG. 6A indicates the omission of exon 17.

As can be seen in FIG. 6A, the frame shift generates a premature stop codon in the κ variant, and so the C-terminal 9 amino acids correspond to the sequence SSGEDGHNE (Seq. ID No. 2 of the attached sequence listing).

Figure 6B:
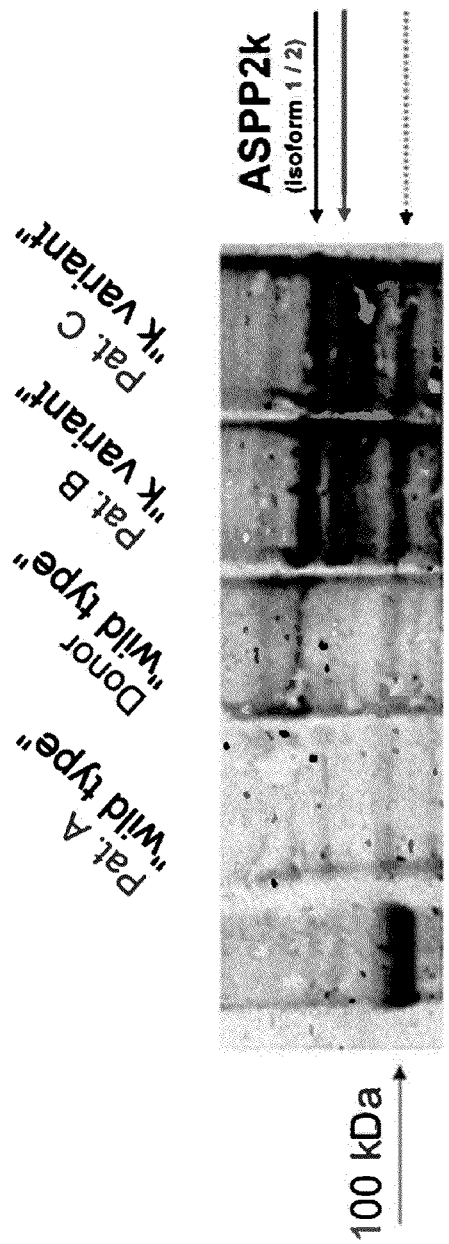

Subsequently, the ASPP2κ variant was then also detected in the blood of patients suffering from acute leukemia by means of Western blotting. The results of these experiments are shown in FIG. 6B. The samples examined came from a healthy donor ("Donor wild type") and from three patients. As can be seen in FIG. 6B, for both patient B and C, there was detection of multiple bands corresponding to ASPP2κ isoforms 1 and 2 (variants of ASPP2isoforms 1 and 2) and presumably at least one further ASPP2 variant, which are likewise greatly shortened with respect to the wild-type isoforms and bear the characteristic sequence SSGEDGHNE (SEQ ID NO: 2).

The ASPP2 wild-type and kappa variants were verified earlier by means of PCR and sequencing for the donor and patients A and B. In the case of patient C, the ASPP2 status was initially unknown; the presence of ASPP2 kappa in patient C was suggested on the basis of the immunoblotting result, and subsequently confirmed by PCR and sequencing.

What is claimed is:

1. A method for the in vitro determination of the presence of cancer in a patient, comprising
measuring the amount of an apoptosis-stimulating protein of p53 (ASPP2) isoform protein using an antibody that specifically binds an epitope consisting of the amino acid sequence set forth as SEQ ID NO: 2 in a biological sample comprising cancer cells from the patient, and
comparing the amount of the epitope present in the biological sample to a control from a healthy subject;
wherein an increase in the amount of the epitope in the biological sample as compared to the control determines that the cancer is present in the patient.

2. The method as claimed in claim 1, wherein the cancer is a hematologic neoplasia or a solid tumor.

3. The method as claimed in claim 1, wherein the cancer is acute myeloid leukemia, chronic myeloid leukemia, or acute lymphoblastic leukemia.

4. A method of diagnosing cancer in a subject, comprising
measuring, in a biological sample comprising cancer cells from the subject, the amount of an ASPP2 isoform protein using an antibody that specifically binds an amino acid molecule consisting of the amino acid sequence of SEQ ID NO: 2, and
comparing the amount of the ASPP2 isoform protein in the biological sample to the amount of the ASPP2 isoform protein in a control sample from a healthy subject;
wherein an increase in the amount of the ASPP2 isoform protein in the biological sample as compared to the control sample indicates that the subject has cancer.

5. A method for the in vitro determination of the presence of cancer in a patient, comprising
measuring an amount of an ASPP2 isoform protein using an antibody that specifically binds an epitope consisting of the amino acid sequence set forth as SEQ ID NO: 2 in a biological sample comprising cancer cells from the patient, wherein measuring the amount of the ASPP2 isoform protein comprises:
a) contacting the biological sample from the patient with the antibody;
b) detecting the presence of the antibody specifically bound to the amino acid sequence set forth as SEQ ID NO: 2; and
c) quantifying the amount of the antibody specifically bound to the amino acid sequence set forth as SEQ ID NO: 2, thereby determining the amount of the ASPP2 isoform protein present in the biological sample,
comparing the amount of the ASPP2 isoform protein present in the biological sample to an amount of the ASPP2 isoform protein present in a control sample from a healthy subject;
wherein an increase in the amount of the ASPP2 isoform protein in the biological sample as compared to the control sample determines that the cancer is present in the patient.

6. The method of claim 4, wherein the cancer is acute or chronic myeloid leukemia.

7. The method as claimed in claim 1, wherein the cancer is acute lymphoblastic leukemia.

8. A method of diagnosing cancer in a subject, comprising
contacting a biological sample comprising cancer cells with an antibody that specifically binds to the amino acid sequence set forth as SEQ ID NO: 2; and
quantifying an amount of the antibody specifically bound to the amino acid sequence set forth as SEQ ID NO: 2 in the biological sample, thereby detecting the amount of the ASPP2 isoform protein present in the biological sample;
comparing the amount of the ASPP2 isoform protein present in the biological sample to a quantity of the ASPP2 isoform protein present in a control sample from a healthy subject;
wherein an increase in the amount of the ASPP2 isoform protein present in the biological sample as compared to the quantity of the ASPP2 isoform protein present in the control sample indicates that the subject has cancer.

9. The method as claimed in claim 4, wherein the cancer is a hematologic neoplasia or a solid tumor.

10. The method as claimed in claim 1, wherein the biological sample is a blood sample.

11. The method as claimed in claim 4, wherein the biological sample is a blood sample.

12. The method as claimed in claim 1, wherein there is an increased amount of the ASPP2 isoform protein in the biological sample from the patient, and wherein the method further comprises administering to the patient an effective amount of a chemotherapeutic agent to treat the cancer.

13. The method as claimed in claim 4, wherein there is an increased amount of the ASPP2 isoform protein in the biological sample from the subject, and wherein the method further comprises administering to the subject an effective amount of a chemotherapeutic agent to treat the cancer.

14. The method as claimed in claim 5, wherein there is an increased amount of the ASPP2 isoform protein in the biological sample from the patient, and wherein the method further comprises administering to the patient an effective amount of a chemotherapeutic agent to treat the cancer.

15. The method as claimed in claim 8, wherein there is an increased amount of the ASPP2 isoform protein in the biological sample from the subject, and wherein the method further comprises administering to the subject an effective amount of a chemotherapeutic agent to treat the cancer.

16. The method as claimed in claim 4, wherein the cancer is acute lymphoblastic leukemia.

\* \* \* \* \*

SEQUENCE LISTING

<160> NUMBER OF SEQ ID NOS: 10

<210> SEQ ID NO 1
<211> LENGTH: 879
<212> TYPE: PRT
<213> ORGANISM: Homo sapiens

<400> SEQUENCE: 1

```
Met Asp Leu Thr Leu Ala Glu Leu Gln Glu Met Ala Ser Arg Gln Gln
1               5                   10                  15

Gln Gln Ile Glu Ala Gln Gln Gln Leu Leu Ala Thr Lys Glu Gln Arg
            20                  25                  30

Leu Lys Phe Leu Lys Gln Gln Asp Gln Arg Gln Gln Gln Gln Val Ala
        35                  40                  45

Glu Gln Glu Lys Leu Lys Arg Leu Lys Glu Ile Ala Glu Asn Gln Glu
    50                  55                  60

Ala Lys Leu Lys Lys Val Arg Ala Leu Lys Gly His Val Glu Gln Lys
65                  70                  75                  80

Arg Leu Ser Asn Gly Lys Leu Val Glu Glu Ile Glu Gln Met Asn Asn
                85                  90                  95

Leu Phe Gln Gln Lys Gln Arg Glu Leu Val Leu Ala Val Ser Lys Val
            100                 105                 110

Glu Glu Leu Thr Arg Gln Leu Glu Met Leu Lys Asn Gly Arg Ile Asp
        115                 120                 125

Ser His His Asp Asn Gln Ser Ala Val Ala Glu Leu Asp Arg Leu Tyr
    130                 135                 140

Lys Glu Leu Gln Leu Arg Asn Lys Leu Asn Gln Glu Gln Asn Ala Lys
145                 150                 155                 160

Leu Gln Gln Gln Arg Glu Cys Leu Asn Lys Arg Asn Ser Glu Val Ala
                165                 170                 175

Val Met Asp Lys Arg Val Asn Glu Leu Arg Asp Arg Leu Trp Lys Lys
            180                 185                 190

Lys Ala Ala Leu Gln Gln Lys Glu Asn Leu Pro Val Ser Ser Asp Gly
        195                 200                 205

Asn Leu Pro Gln Gln Ala Ala Ser Ala Pro Ser Arg Val Ala Ala Val
    210                 215                 220
```

-continued

```
Gly Pro Tyr Ile Gln Ser Ser Thr Met Pro Arg Met Pro Ser Arg Pro
225                 230                 235                 240

Glu Leu Leu Val Lys Pro Ala Leu Pro Asp Gly Ser Leu Val Ile Gln
            245                 250                 255

Ala Ser Glu Gly Pro Met Lys Ile Gln Thr Leu Pro Asn Met Arg Ser
        260                 265                 270

Gly Ala Ala Ser Gln Thr Lys Gly Ser Lys Ile His Pro Val Gly Pro
    275                 280                 285

Asp Trp Ser Pro Ser Asn Ala Asp Leu Phe Pro Ser Gln Gly Ser Ala
290                 295                 300

Ser Val Pro Gln Ser Thr Gly Asn Ala Leu Asp Gln Val Asp Asp Gly
305                 310                 315                 320

Glu Val Pro Leu Arg Glu Lys Glu Lys Lys Val Arg Pro Phe Ser Met
            325                 330                 335

Phe Asp Ala Val Asp Gln Ser Asn Ala Pro Pro Ser Phe Gly Thr Leu
        340                 345                 350

Arg Lys Asn Gln Ser Ser Glu Asp Ile Leu Arg Asp Ala Gln Val Ala
    355                 360                 365

Asn Lys Asn Val Ala Lys Val Pro Pro Val Pro Thr Lys Pro Lys
370                 375                 380

Gln Ile Asn Leu Pro Tyr Phe Gly Gln Thr Asn Gln Pro Pro Ser Asp
385                 390                 395                 400

Ile Lys Pro Asp Gly Ser Ser Gln Gln Leu Ser Thr Val Val Pro Ser
            405                 410                 415

Met Gly Thr Lys Pro Lys Pro Ala Gly Gln Gln Pro Arg Val Leu Leu
        420                 425                 430

Ser Pro Ser Ile Pro Ser Val Gly Gln Asp Gln Thr Leu Ser Pro Gly
    435                 440                 445

Ser Lys Gln Glu Ser Pro Pro Ala Ala Ala Val Arg Pro Phe Thr Pro
450                 455                 460

Gln Pro Ser Lys Asp Thr Leu Leu Pro Pro Phe Arg Lys Pro Gln Thr
465                 470                 475                 480

Val Ala Ala Ser Ser Ile Tyr Ser Met Tyr Thr Gln Gln Gln Ala Pro
            485                 490                 495

Gly Lys Asn Phe Gln Gln Ala Val Gln Ser Ala Leu Thr Lys Thr His
        500                 505                 510

Thr Arg Gly Pro His Phe Ser Ser Val Tyr Gly Lys Pro Val Ile Ala
    515                 520                 525

Ala Ala Gln Asn Gln Gln Gln His Pro Glu Asn Ile Tyr Ser Asn Ser
530                 535                 540

Gln Gly Lys Pro Gly Ser Pro Glu Pro Glu Thr Glu Pro Val Ser Ser
545                 550                 555                 560

Val Gln Glu Asn His Glu Asn Glu Arg Ile Pro Arg Pro Leu Ser Pro
            565                 570                 575

Thr Lys Leu Leu Pro Phe Leu Ser Asn Pro Tyr Arg Asn Gln Ser Asp
        580                 585                 590

Ala Asp Leu Glu Ala Leu Arg Lys Lys Leu Ser Asn Ala Pro Arg Pro
    595                 600                 605

Leu Lys Lys Arg Ser Ser Ile Thr Glu Pro Glu Gly Pro Asn Gly Pro
610                 615                 620

Asn Ile Gln Lys Leu Leu Tyr Gln Arg Thr Thr Ile Ala Ala Met Glu
625                 630                 635                 640
```

```
Thr Ile Ser Val Pro Ser Tyr Pro Ser Lys Ser Ala Ser Val Thr Ala
                645                 650                 655

Ser Ser Glu Ser Pro Val Glu Ile Gln Asn Pro Tyr Leu His Val Glu
            660                 665                 670

Pro Glu Lys Glu Val Val Ser Leu Val Pro Glu Ser Leu Ser Pro Glu
        675                 680                 685

Asp Val Gly Asn Ala Ser Thr Glu Asn Ser Asp Met Pro Ala Pro Ser
    690                 695                 700

Pro Gly Leu Asp Tyr Glu Pro Glu Gly Val Pro Asp Asn Ser Pro Asn
705                 710                 715                 720

Leu Gln Asn Asn Pro Glu Glu Pro Asn Pro Glu Ala Pro His Val Leu
                725                 730                 735

Asp Val Tyr Leu Glu Glu Tyr Pro Pro Tyr Pro Pro Pro Tyr Pro
            740                 745                 750

Ser Gly Glu Pro Glu Gly Pro Gly Glu Asp Ser Val Ser Met Arg Pro
            755                 760                 765

Pro Glu Ile Thr Gly Gln Val Ser Leu Pro Pro Gly Lys Arg Thr Asn
        770                 775                 780

Leu Arg Lys Thr Gly Ser Glu Arg Ile Ala His Gly Met Arg Val Lys
785                 790                 795                 800

Phe Asn Pro Leu Ala Leu Leu Leu Asp Ser Ser Leu Glu Gly Glu Phe
                805                 810                 815

Asp Leu Val Gln Arg Ile Ile Tyr Glu Val Asp Asp Pro Ser Leu Pro
            820                 825                 830

Asn Asp Glu Gly Ile Thr Ala Leu His Asn Ala Val Cys Ala Gly His
            835                 840                 845

Thr Glu Ile Val Lys Phe Leu Val Gln Phe Gly Val Asn Val Asn Ala
        850                 855                 860

Ala Asp Ser Asp Gly Trp Ser Ser Gly Glu Asp Gly His Asn Glu
865                 870                 875

<210> SEQ ID NO 2
<211> LENGTH: 9
<212> TYPE: PRT
<213> ORGANISM: Homo sapiens

<400> SEQUENCE: 2

Ser Ser Gly Glu Asp Gly His Asn Glu
1               5

<210> SEQ ID NO 3
<211> LENGTH: 3451
<212> TYPE: DNA
<213> ORGANISM: Homo sapiens

<400> SEQUENCE: 3 gctgggccc  gacccgggat  tagttggttt  cggagcggag  gagggagccc  cgaccgtcac     60
gagcgtcgaa  gagacaaagc  cgcgtcaggg  ggcccggccg  ggcggggga  gcccggggct    120 tgttggtgcc  ccagcccgcg  cggagggccc  ttcggacccg  cgcgccgccg  ctgccgccgc    180
cgccgcctcg  caacaggtcc  gggcggcctc  gctctccgct  cccctccccc  gcatccgcga    240
ccctccgggg  cacctcagct  cggccggggc  cgcagtctgg  ccacccgctt  ccatgcggtt    300
cgggtccaag  atgatgccga  tgtttcttac  cgtgtatctc  agtaacaatg  agcagcactt    360
cacagaagtt  ccagttactc  cagaaacaat  atgcagagac  gtggtggatc  tgtgcaaaga    420
acccggcgag  agtgattgcc  atttggctga  agtgtggtgt  ggctctgtag  agatagagtt    480
```

```
tcatcatgtt ggccaggatg gtctcgatct cctgaccttg tgatccgcct gcctcggcct      540
cccaaagtgc tggattacag gtgtgagcca ccacgatcag cctctagtgt ttaaaaaaga      600
acgtccagtt gcggataatg agcgaatgtt tgatgttctt caacgatttg aagtcagag       660 gaacgaagtt cgcttcttcc ttcgtcatga acgcccccct ggcagggaca ttgtgagtgg      720
accaagatct caggatccaa gtttaaaaag aaatggtgta aaagttcctg gtgaatatcg      780
aagaaaggag aacggtgtta atagtcctag gatggatctg actcttgctg aacttcagga      840
aatggcatct cgccagcagc aacagattga agcccagcaa caattgctgg caactaagga      900
acagcgctta aagtttttga acaacaaga tcagcgacaa cagcaacaag ttgctgagca       960
ggagaaactt aaaaggctaa agaaatagc tgagaatcag gaagctaagc taaaaaaagt     1020
gagagcactt aaaggccacg tggaacagaa gagactaagc aatgggaaac ttgtggagga     1080
aattgaacag atgaataatt tgttccagca aaaacagagg gagctcgtcc tggctgtgtc     1140
aaaagtagaa gaactgacca ggcagctaga gatgctcaag aacggcagga tcgacagcca     1200
ccatgacaat cagtctgcag tggctgagct tgatcgcctc tataaggagc tgcagctaag     1260
aaacaaattg aatcaagagc agaatgccaa gctacaacaa cagagggagt gtttgaataa     1320
gcgtaattca gaagtggcag tcatggataa gcgtgttaat gagctgaggg accggctgtg     1380
gaagaagaag gcagctctac agcaaaaaga aaatctacca gtttcatctg atggaaatct     1440
tccccagcaa gccgcgtcag ccccaagccg tgtggctgca gtaggtccct atatccagtc     1500
gtctactatg cctcggatgc cctcaaggcc tgaattgctg gtgaagccag ccctgccgga     1560
tggttccttg gtcattcagg cttcagaggg gccgatgaaa atacagacac tgcccaacat     1620
gagatctggg gctgcttcac aaactaaagg ctctaaaatc catccagttg gccctgattg     1680
gagtccttca aatgcagatc ttttcccaag ccaaggctct gcttctgtac ctcaaagcac     1740
tgggaatgct ctggatcaag ttgatgatgg agaggttccg ctgagggaga agagaagaa      1800 agtgcgtccg ttctcaatgt tgatgcagt agaccagtcc aatgccccac cttcctttgg      1860
tactctgagg aagaaccaga gcagtgaaga tatcttgcgg gatgctcagg ttgcaaataa     1920
aaatgtggct aaagtaccac ctcctgttcc tacaaaacca aaacagatta atttgcctta     1980
ttttggacaa actaatcagc caccttcaga cattaagcca gacggaagtt ctcagcagtt     2040
gtcaacagtt gttccgtcca tgggaactaa accaaaacca gcagggcagc agccgagagt     2100
gctgctatct cccagcatac cttcggttgg ccaagaccag acccttctct caggttctaa     2160
gcaagaaagt ccacctgctg ctgccgtccg gcccttact cccagccctt ccaaagacac      2220
cttacttcca cccttcagaa aaccccagac cgtggcagca gttcaatat attccatgta      2280 tacgcaacag caggcgccag gaaaaaactt ccagcaggct gtgcagagcg cgttgaccaa     2340
gactcatacc agagggccac acttttcaag tgtatatggt aagcctgtaa ttgctgctgc     2400
ccagaatcaa cagcagcacc cagagaacat ttattccaat agccagggca agcctggcag     2460
tccagaacct gaaacagagc ctgtttcttc agttcaggag aaccatgaaa acgaaagaat     2520
tcctcggcca ctcagcccaa ctaaattact gcctttctta tctaatcctt accgaaacca     2580
gagtgatgct gacctagaag ccttacgaaa gaaactgtct aacgcaccaa ggcctctaaa     2640
gaaacgtagt tctattacag agccagaggg tcctaatggg ccaaatattc agaagctttt     2700
atatcagagg accaccatag cggccatgga gaccatctct gtcccatcat acccatccaa     2760
gtcagcttct gtgactgcca gctcagaaag cccagtagaa atccagaatc catatttaca     2820
```

```
tgtggagccc gaaaaggagg tggtctctct ggttcctgaa tcattgtccc cagaggatgt    2880
ggggaatgcc agtacagaga acagtgacat gccagctcct tctccaggcc ttgattatga    2940
gcctgaggga gtcccagaca acagcccaaa tctccagaat aacccagaag aaccaaatcc    3000
agaggctcca catgtgcttg atgtgtacct ggaggagtac cctccatacc cacccccacc    3060
atacccatct ggggagcctg aagggcccgg agaagactcg gtgagcatgc gcccgcctga    3120
aatcaccggg caggtctctc tgcctcctgg taaaaggaca aacttgcgta aaactggctc    3180
agagcgtatc gctcatggaa tgagggtgaa attcaacccc cttgctttac tgctagattc    3240
gtctttggag ggagaatttg accttgtaca gagaattatt tatgaggttg atgacccaag    3300
cctccccaat gatgaaggca tcacggctct tcacaatgct gtgtgtgcag ccacacaga     3360 aatcgttaag ttcctggtac agtttggtgt aaatgtaaat gctgctgata gtgatggatg    3420
gagttcagga gaagatgggc ataatgaata a                                   3451

<210> SEQ ID NO 4
<211> LENGTH: 59
<212> TYPE: DNA
<213> ORGANISM: Homo sapiens

<400> SEQUENCE: 4
tgctgctgat agtgatggat ggagttcagg agaagatggg cataatgaat aaaggagtc       59

<210> SEQ ID NO 5
<211> LENGTH: 59
<212> TYPE: DNA
<213> ORGANISM: Homo sapiens

<400> SEQUENCE: 5
acgacgacta tcactaccta cctcaagtcc tcttctaccc gtattactta tttcctcag       59

<210> SEQ ID NO 6
<211> LENGTH: 16
<212> TYPE: PRT
<213> ORGANISM: Homo sapiens

<400> SEQUENCE: 6

Met Leu Leu Ile Val Met Asp Ser Ser Gly Glu Asp Gly His Asn Glu
1               5                   10                  15

<210> SEQ ID NO 7
<211> LENGTH: 18
<212> TYPE: PRT
<213> ORGANISM: Homo sapiens

<400> SEQUENCE: 7

Lys Cys Cys Trp Met Gly Val Gln Glu Lys Met Gly Ile Met Asn Lys
1               5                   10                  15

Gly Val

<210> SEQ ID NO 8
<211> LENGTH: 19
<212> TYPE: PRT
<213> ORGANISM: Homo sapiens

<400> SEQUENCE: 8

Asn Ala Ala Asp Ser Asp Gly Trp Glu Phe Arg Arg Arg Trp Ala Ile
1               5                   10                  15

Lys Glu Ser
```

```
<210> SEQ ID NO 9
<211> LENGTH: 74
<212> TYPE: DNA
<213> ORGANISM: Homo sapiens

<400> SEQUENCE: 9
tgtaaatgta aatgctgctg atagtgatgg atggastyca tkacattgtg gtgcctcwgg      60
aaacaacatc catt                                                        74

<210> SEQ ID NO 10
<211> LENGTH: 74
<212> TYPE: DNA
<213> ORGANISM: Homo sapiens

<400> SEQUENCE: 10
cctttattca ttatgcccat cttctcctga actccatmma kaamttggga gmrctgtgtg      60
tagccttcct ccat                                                        74
```